United States Patent [19]

Holland et al.

[11] Patent Number: 4,510,095
[45] Date of Patent: Apr. 9, 1985

[54] PRODUCTION OF ORGANOTIN HALIDES

[75] Inventors: Frank S. Holland, Hazel Grove; Peter Womersley, Heaton Mersey; John Curran, Clayton, all of England

[73] Assignee: Manchem Limited, Manchester, England

[21] Appl. No.: 456,316

[22] Filed: Jan. 6, 1983

[30] Foreign Application Priority Data

Jan. 7, 1982 [GB] United Kingdom ............... 8200353

[51] Int. Cl.³ .............................................. C07F 7/22
[52] U.S. Cl. ................................ 260/429.7; 204/159
[58] Field of Search ........................ 260/429.7; 204/159

[56] References Cited

U.S. PATENT DOCUMENTS

| 3,415,857 | 12/1968 | Hoye | 260/429.7 |
| 3,519,665 | 7/1970 | Molt et al. | 260/429.7 |
| 3,651,108 | 3/1972 | Giannaccari et al. | 260/429.7 |
| 3,745,183 | 7/1973 | Katsumura et al. | 260/429.7 |
| 3,857,868 | 12/1974 | Witman et al. | 260/429.9 |
| 3,970,679 | 7/1976 | Jung et al. | 260/429.7 |
| 3,975,417 | 8/1976 | Sagawa et al. | 260/429.7 |
| 4,129,584 | 12/1978 | Reifenberg | 260/429.7 |
| 4,179,458 | 12/1979 | Jones | 260/429.7 |

Primary Examiner—Helen M. S. Sneed
Attorney, Agent, or Firm—Cushman, Darby & Cushman

[57] ABSTRACT

A process is disclosed for the direct production of organotin halides, particularly triorganotin halides by the reaction of elemental tin and an organotin halide in the presence of a reagent amount of an 'onium compound of the general formula $Cat^+X^-$. $Cat^+X^-$ may represent a quaternary ammonium or phosphonium group or a ternary sulphonium group, or may also represent a complex of an alkali metal or alkaline earth metal with a polyoxygen compound. High yields of triorganotin halide product are obtained in contrast to results of reactions wherein $Cat^+X^-$ is present in only catalytic amounts.

16 Claims, 5 Drawing Figures

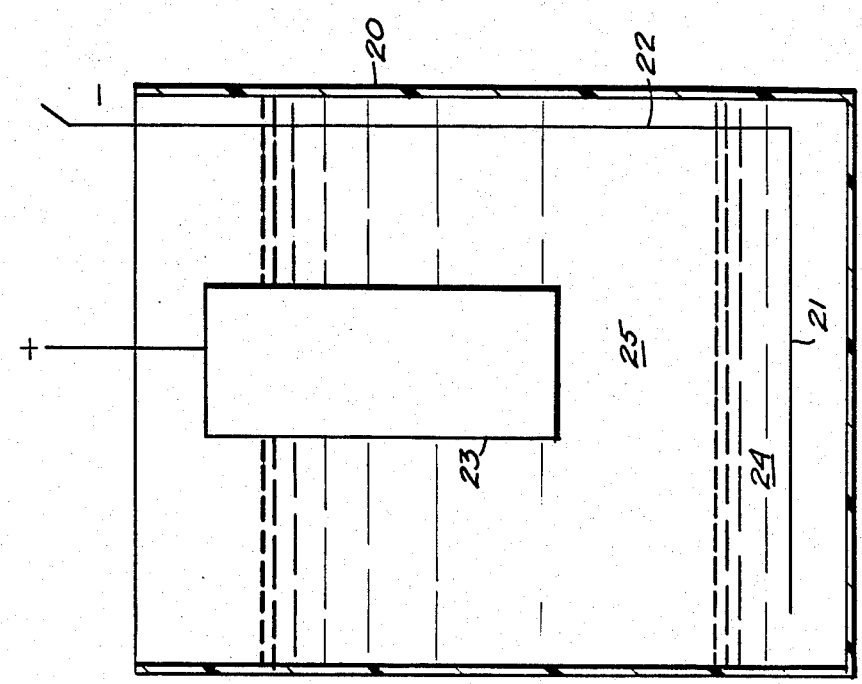
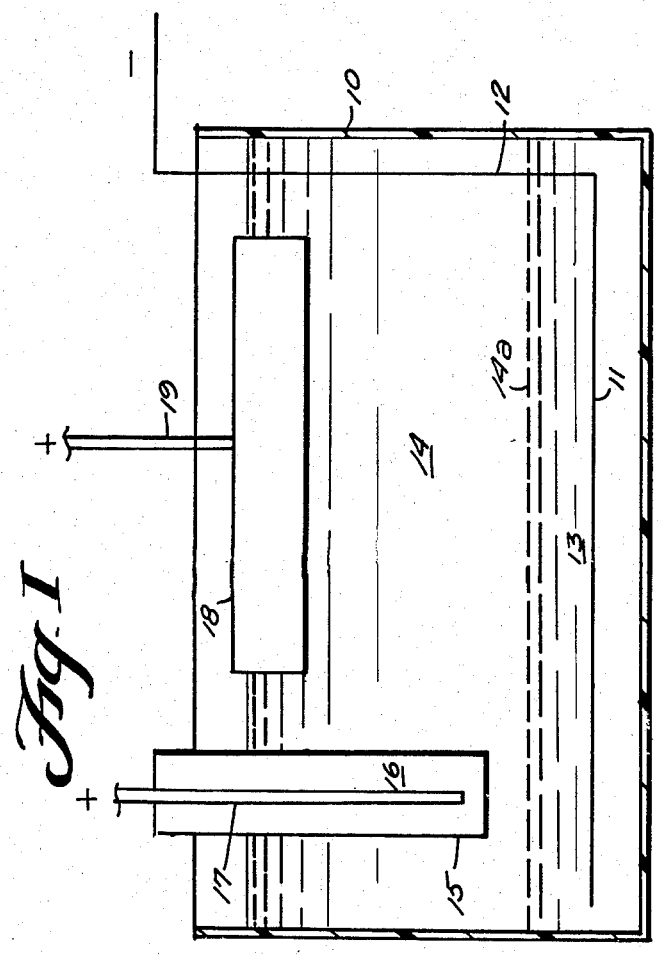
Fig. I
Fig. II

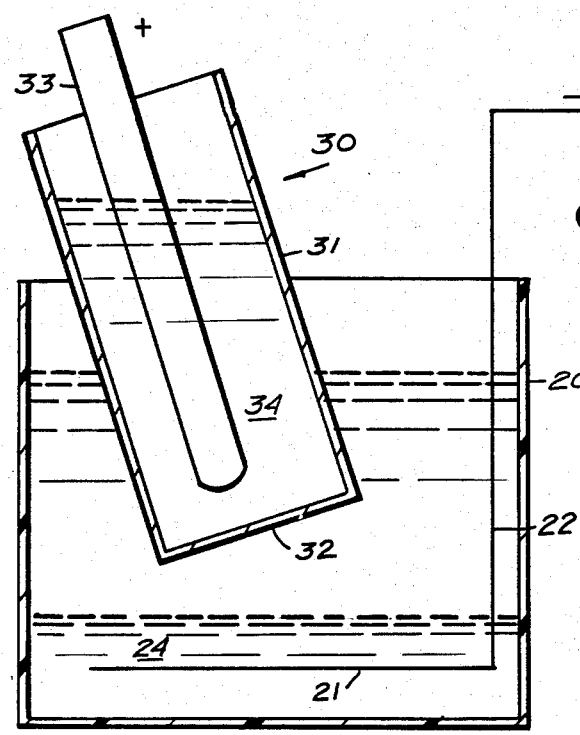
Fig. III
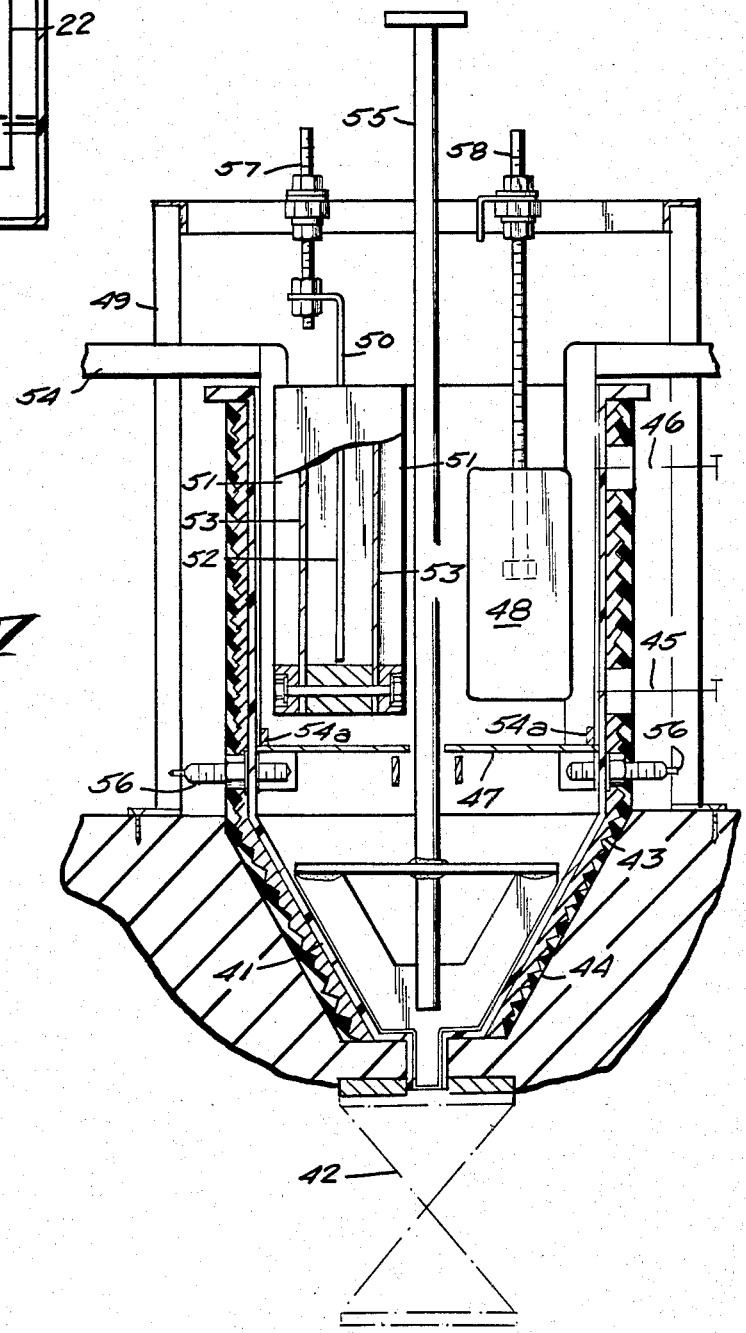
Fig. IV

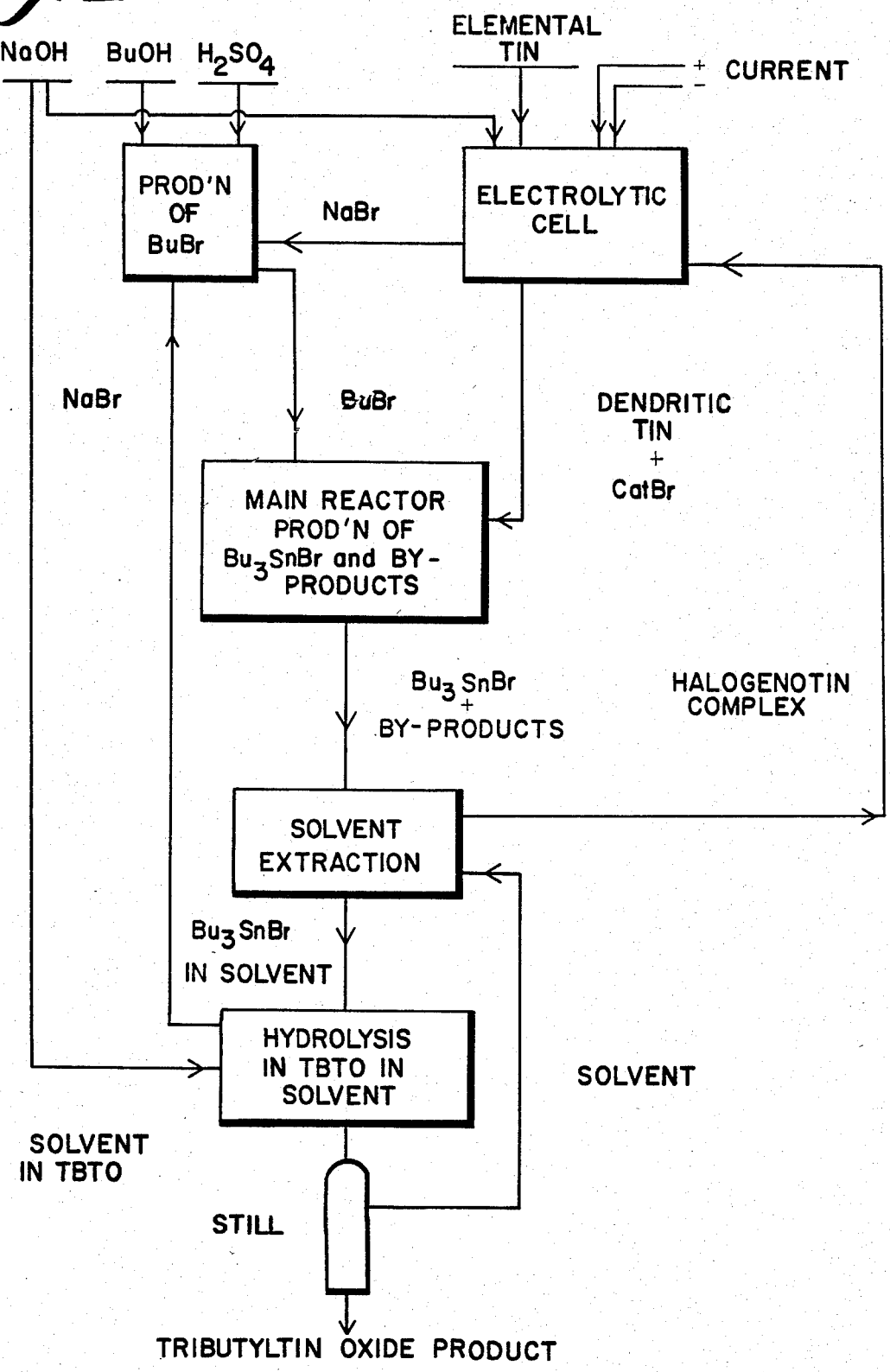
Fig. V

PRODUCTION OF ORGANOTIN HALIDES

This invention relates to the production of organotin halides, and provides a process for the direct reaction of elemental tin with organic halides to produce organotin halides which are predominantly triorganotin halides.

BACKGROUND OF THE INVENTION

Conventional processes for the production of triorganotin monohalides usually involve reacting the corresponding tetraorganotin compound with stannic chloride; the tetraorganotin being initially made via a Grignard process or an aluminum alkyl process.

However, these are inefficient, multistage, indirect, processes, and various investigators have searched for direct processes. British patent specifications Nos. 1,432,047 and 1,450,490 describe processes which attempt to control the Grignard process and stop the reaction at the stage when three carbon-to-tin bonds are formed. Such control is very difficult to achieve. U.S. Pat. Nos. 3,471,539 and 3,475,472 describe processes for adding a third carbon-tin bond to a pre-formed diorganotin compound using another metal (e.g., zinc), i.e., $$R_2SnX_2 + RX + Zn \rightarrow R_3SnX + ZnX_2.$$

Another U.S. Pat. No. 3,547,965 describes a process for the direct preparation of triorganotin halides using a stoichiometric amount of zinc, i.e., $$3RX + Sn + Zn \rightarrow R_3SnX + ZnX_2.$$

Still another U.S. Pat. No. 2,852,543 describes a process using two additional metals (sodium and zinc) which can produce a mixture of tri- and tetraorganotins and which is mainly triorganotin.

All of these processes involve another metal, as well as tin, and therefore do not offer any real advantage over the traditional multistage processes.

As mentioned earlier, tetraorganotin compounds are commonly made via a Grignard process, or an aluminum alkyl process. Less common processes use molten sodium. In all of these cases the tin is usually present as the tetrahalide, e.g., the tetrachloride. However, direct processes to make tetraorganotins from elemental tin have also been described.

Thus U.S. Pat. No. 3,651,108 describes the preparation of tetraorganotin compounds by reaction of organic halides in the presence of an 'onium compound, or Lewis base, with tin and an alkali or alkaline earth metal, in particular magnesium. Similarly U.S. Pat. Nos. 4,179,458 and 4,092,340 describe processes for preparing tetraorganotin compounds which comprise reacting an organic halide of formula RX with a heated suspension of metallic material which is zinc and tin (in the atomic preparations of at least 0.5 to 1) in a liquid comprising at least one 'onium salt, which salt is an organic quaternary ammonium or phosphonium or tertiary sulphonium salt, to produce the tetraorganotin compound. In U.S. Pat. No. 4,179,458 this agent is a liquid, in U.S. Pat. No. 4,092,340, it is a gas. From the examples given in these two cases, the processes appear to be $$4RX + Sn + 2Zn \rightarrow R_4Sn + 2ZnX_2.$$

The liquid 'onium compound functions as a solvent.

Both specifications state that the tetraorganotin product may be used for preparing triorganotin halo compounds by mixing with the appropriate molar proportion of stannic halide, e.g., stannic chloride.

Direct processes (i.e., involving tin only as the metal) for the production of diorganotin compounds are well known. For example see a review article by Murphy & Poller, The Preparation of Organotin Compounds by the Direct Reaction, *J. Organomet. Chem. Lib.*, (1979), 9, 189–222.

The direct reaction of tin with an organic halide in the presence of catalytic amounts of a quaternary ammonium and phosphonium compound or of a ternary sulphonium or isosulphonium compound to produce primarily mono- and diorganotin halides (possibly with triorganotin halides as a minor product) is disclosed in several earlier patent specifications, for example, British specifications Nos. 1,115,646, 1,053,996 and 1,222,642, the respective disclosures of which are incorporated herein by reference.

Specification No. 1,115,646 discloses reacting metallic tin (which may be used in powder, sheet or granule form, and may be part of an alloy, especially with a co-catalyst) with an aliphatic halide in the presence of a catalyst, which is an 'onium compound (defined as a compound containing organic groups covalently bonded to a positively charged non-metallic atom from Group V or VI of the periodic table, and exemplified by tetraalkylammonium halides, tetraalkyl phosphonium halides and trialkylsulphonium halides) and in the presence of a preformed stannous halide or pre-formed organotin halide, and optionally in the presence of a small amount of a co-catalyst which is one of thirteen defined metals (said small amount being up to 0.1 mole per gram-atom of tin). The product of the reaction of Specification No. 1,115,646 is a mixture of organotin halides in which the diorganotin dihalide predominates.

General Description of the Invention

The invention is particularly concerned with the production of triorganotin monohalides, that is, compounds of the formula $R_3SnX$, in which each of the three R's, independently of the others, is an organic group, especially a hydrocarbyl group preferably containing up to 20 carbon atoms selected from the class of alkyl (including cycloalkyl, alkenyl, aralkyl, aryl and aralkenyl groups) and X is a halogen atom selected from chlorine, bromine and iodine.

We have now discovered a process using the direct reaction of tin with an organic halide (RX) in the presence of a compound such as an 'onium compound, hitherto known and used as a catalyst, which forms a product consisting almost wholly, or at least predominantly, of triorganotin halide, provided that such compound is used in much greater than a catalytic amount, i.e., in reagent amount, and is in effect used as the reaction solvent.

In addition to the following description, the invention is further illustrated by the accompanying drawings (which in part pertain to separate inventions by one of us disclosed in applications entitled "Electrolysis of Tin Complexes" and "Electrolysis Using Two Electrolytically Conducting Phases" filed of even date herewith, the respective disclosures of which are incorporated herein by reference):

FIG. 1 schematically illustrates a double anode cell used in one mode of practice of this invention (detailed description in Example 5);

FIG. II schematically illustrates a second electrolytic cell which may be used in another embodiment (detailed description in Example 6);

FIG. III schematically illustrates still a further electrolysis cell embodiment (detailed description also in Example 6);

FIG. IV illustrates a still further electrolytic cell embodiment (detailed description in Example 12);

FIG. V illustrates an overall flow sheet of one embodiment of the cyclic process of this invention (detailed description in Example 10).

The 'onium reagent which may be used according to our discovery is in general terms, a compound of the formula Cat$^+$X$^-$, wherein Cat$^+$ is a positively charged species and X$^-$ is chloride, bromide or iodide. When Cat$^+$ is a quaternary ammonium or phosphonium group or a ternary sulphonium group, the compound is an 'onium salt as defined in U.K. specification No. 1,115,646. A second metal, i.e., a metal other than tin, may optionally be present in limited amount, as defined in specification No. 1,115,646, but is not essential. A pre-formed tin compound is not an essential participant in the process but a pre-formed organotin halide may optionally be present. Further, if a pre-formed mono- or diorganotin halide is present, it will largely be converted to triorganotin halide, provided that the compound of formula Cat$^+$X$^-$ is used in reagent amount.

A theoretical stoichiometry in the reaction in our process (but not necessarily representative of any actual reaction scheme) can be represented thus:

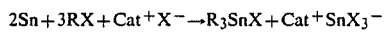

For example, when butyl bromide is the organic halide and tetrabutylammonium bromide is the reagent, the stoichiometry is represented by

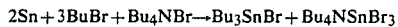

wherein Bu represents butyl.

It will be noted that in the process of U.K. No. 1,115,646 the tin essentially either forms the there-desired diorganotin halide or remains as unreacted tin, because the 'onium is present in only catalytic amount. By contrast in the process of the present invention part of the tin forms the presently-desired triorganotin halide, while approximately a stoichiometric amount is also complexed with, e.g., an 'onium reagent.

We have indeed found that when the quantity of the 'onium reagent relative to the quantity of organic halide is as high as 1:3, or higher, on a molar basis, as required by the foregoing stoichiometry, the organotin product can be substantially 100% triorganotin halide. However, even when the molar ratio of reagent to organic halide is somewhat lower than this, e.g., 1:4, the organotin product can still contain as much as 95% triorganotin. If the molar ratio is still lower, e.g., 1:5, there will still be more than 50%, on a molar basis, of triorganotin halide in the organotin product. Thus the reaction appears to be more complex in fact than is suggested by the simple reaction scheme above.

The effect of the high concentration of the 'onium reagent (from here on when referring to "reagent", we mean the compound of the general formula Cat$^+$X$^-$) appears to be to make available halide ions which form complex anions with tin, and these complexes effect nucleophilic attack on the organic halide. The halide ions appear to act as nucleophile generators. A possible partial reaction scheme which might explain how our process works is shown below, for the case where the halide is bromide and the organic group is butyl (i.e., Bu):

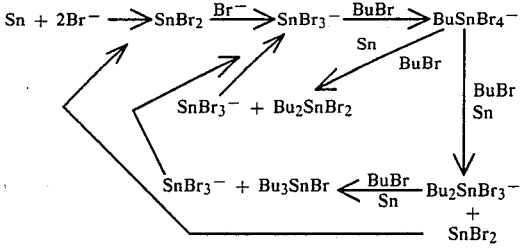

The positively charged 'onium species of formula Cat$^+$ may also be a complex of an alkali metal or alkaline earth metal with a polyoxygen compound such as diglyme, a polyalkylene glycol or glycol ether, or a crown ether. Alternatively, the positively charged species can be of the formula R'$_z$Q$^+$ where R' is an organic group (conveniently hydrocarbyl as defined above, and including di-valent alkylene or oxyalkylene radicals to form a heterocyclic ring with Q), and Q is N, P, As or Sb in which case z is 4 or Q is S or Se in which case z is 3. The quaternary ammonium and phosphonium compounds and the ternary sulphonium and isosulphonium compounds disclosed only as catalysts in U.K. No. 1,115,646 are thus available here as reagents for use in the present invention.

As already noted, the use of Cat$^+$X$^-$ system as described in earlier patent specifications leads to the formation of mainly diorganotin dihalides, but intriguingly some of these also describe the formulation of some triorganotin halide as by-product. Since the discovery of the present invention, it might now be expected, with hindsight, that in these earlier disclosures there would be found some correlation between the amount of Ca$^+$X$^-$ used and the amount of triorganotin halide produced. However, this is not so; indeed, a detailed examination shows a confused and complex picture.

From the theoretical stoichiometry in the reaction in our process

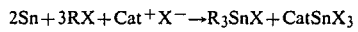

one might expect the ratio of R$_3$SnX to Cat$^+$X$^-$ to be one. In the various examples given in U.K. specification No. 1,053,996, this ratio ranges from 0 to 2.25. In the examples given in U.K. specification No. 1,115,646 the ratio ranges from 0 to 0.7 (even in very similar examples). In the examples given in U.K. specification No. 1,222,642, no R$_3$SnX is apparently formed. For the examples given in U.K. specification No. 1,276,321 no yield of R$_3$SnX is reported, and the products are described as substantially R$_2$SnX$_2$. In the one example describing any R$_3$SnX formation in U.K. specification No. 1,440,156, the ratio is 0.1; apparently the other examples produced R$_2$SnX$_2$ only. In the examples given in U.S. Pat. No. 3,711,524 diorganotin dihalides are the only product. In the examples given in U.K. specification No. 1,118,170 (which uses an alkali metal-polyoxygen compound to make the positively charged species Cat$^+$) the ratio ranges from 0 to 0.35.

Thus previous disclosures are not consistent with the theoretical simple reaction scheme; apparently other reactions may also be occurring. For example a parallel reaction not involving Cat+X− may occur as follows:

$$2Sn + 3RX \rightarrow R_3SnX + SnX_2$$

In this case the SnX$_2$ produced might combine with the CatSnX$_3$ to give CatSn$_2$X$_5$. (Such species are themselves known, see Birch, Donaldson, and Silver, J. Chem. Soc., Dalton, 1972, 1950-53.) A further possible reaction might be:

$$4Sn + 6RX + Cat^+X^- \rightarrow 2R_3SnX + Cat^+Sn_2X_5^-.$$

Thus when butyl bromide is the organic halide and tetrabutylammonium bromide is the reagent, one could have $$2Sn + 3BuBr + Bu_4NBr \rightarrow Bu_3SnBr + Bu_4NSnBr_3$$

and $$4Sn + 6BuBr + Bu_4NBr \rightarrow 2Bu_3SnBr + Bu_4NSn_2Br_5$$

Bu$_4$NSnBr$_3$ contains 19.6% tin, whereas Bu$_4$Sn$_2$Br$_5$ contains 27% tin. When operating our present process in open exposure to air, a yellow by-product is commonly found containing 22–23% tin which might conceivably be explained after the fact as a mixture of the above materials. However, this would still fail to explain the conflicting and wide ranging results given in the previous disclosures.

Significantly we have found that we obtain very high yields of the triorganotin halide when operating our process with some excess tin present (i.e., more than 2 mole tin per 3 mole RX, e.g., 2.2 mole) and by the adding of RX to the molten Cat+X− tin-products mixture at such a rate and temperature that the majority is consumed rapidly. We have also found that in the absence of air, the reaction mixture (for the preparation of Bu$_3$SnBr) is very nearly white, rather than yellow, and that the by-product is very pale yellow to white at first but becomes more yellow on exposure to air and light. Again, these by-products contain 21–23 percent tin. In our reaction mixtures we have a very high initial halide ion concentration and the processes occurring might be explained by an initial tin corrosion process which (in the case of Bu$_4$NBr, Sn and BuBr) produces SnBr, SnBr$_2$, SnBr$_3^-$ and SnBr$_4^=$. This might then be followed by the reactions:

$$(Bu_4N)_2SnBr_4 + BuBr + Sn \rightarrow (Bu_4N)_2BuSn_2Br_5$$

$$(Bu_4N)_2BuSn_2Br_5 + BuBr \rightarrow (Bu_4N)_2Bu_2Sn_2Br_6$$

$$(Bu_4N)_2Bu_2Sn_2Br_6 + BuBr + Sn \rightarrow Bu_3SnBr + (Bu_4N)_2Sn_2Br_6$$

The final bromotin complex by-product (Bu$_4$N)$_2$Sn$_2$Br$_6$ which may be white, may decompose to the yellow Bu$_4$NSnBr$_3$. It will contain the initial tin compound giving it the higher tin content. The overall process requires more than two moles of tin since some is required for the initiation process. These suggested compounds are more likely to exist in the conditions of our process since there are high concentrations of halide and halogenotin complexes and only a small dilution by the organic halide (RX). If, on the other hand there is a low concentration of halide and a large dilution by RX then these suggested compounds would probably not be stable and probably not be formed. Instead we would expect the formation of such species as for example Bu$_4$NSnBr$_3$, Bu$_4$NBuSnBr$_4$ which have been described as catalysts for the preparation of diorganotins. Thus, this may, after the fact, explain the sharply different results of our process and the processes of the prior art.

Practices According to this Invention

According to the practice of this invention, the reactant compound of the formula Cat+X− is at least initially present in a quantity sufficient to act as the reaction solvent. Because of the relatively high boiling point of Cat+X−, this permits the attainment of relatively high reaction temperatures. Moreover, the hydrocarbyl halide which is introduced for reaction with the tin is introduced time-wise so that at any given point in time the amount of the unreacted hydrocarbyl halide present in the reaction mixture is of a relatively minor amount. It will be appreciated that if a major or substantial amount of the hydrocarbyl halide were present, it would then serve as a solvent diluent with a possible corresponding decrease in reaction temperature otherwise permitted, and would further dilute the reaction medium, with the combined effect thereof being that the desired formation of the triorganotin halide would either be suppressed or obviated entirely.

It is therefore important for the practice of the present invention that during the course of the reaction the hydrocarbyl halide reagent is introduced over a period of time and at a rate such that it is only present in an amount insufficient to function effectively as a solvent for the reaction mass.

Of course, as the present reaction proceeds, i.e., with the formation of complex hydrocarbyl tin halide compounds and complexes, the reaction medium includes those materials as well, with a corresponding proportional reduction in the concentration of the Cat+X− reagent which was initially present as the sole salt reaction solvent medium. Such additional tin compounds include not only the desired triorganotin halide product, but also various possible intermediate products such as Cat+R$_2$SnX$_3^-$. Notwithstanding the formation of these tin-containing complexes, the absolute quantity of the Cat+X− material, either as such or in a complex form, remains present in the system in sufficient reagent amount to allow the reaction to proceed to form still additional triorganotin halide products. Thus, a continuing condition of the reaction is that preferably the free hydrocarbyl halide reactant is at all times present in at most both a minor weight and molar amount.

It is now believed that one reason why the prior art techniques generally failed to produce the desired trihydrocarbyltin halide products in more than a minor amount of the overall product may have been the failure to restrict the relative amount of hydrocarbyl halide reactant present at any given time in the reaction mixture. Generally speaking, it appears that in the prior art the hydrocarbyl halide reaction was present in large stoichiometric excess with respect to the tin reactant; accordingly those reactions were effectively conducted in the presence of such hydrocarbyl halide also functioning as the reaction solvent.

Thus the present invention provides a process for the production of organotin halides of the general formula R$_a$SnX$_{(4-a)}$ (wherein each R, independently of the others, is an organic radical, X is iodine, chlorine or bromine, and a is a number from 1 to 3 and comprising predominantly triorganotin halides, by the direct reaction of tin (which may be introduced as elemental tin or as a tin alloy) with an organic halide of the formula RX and with a compound of formula $Cat^+X^-$. Optionally, there may be present a second metal (which may be alloyed with elemental tin) in an amount up to 0.1 gram-atom of the second metal per gram-atom of tin, and optionally also the process may be conducted in the presence of a preformed organotin halide of the formula $RSnX_3$ and/or $R_2SnX_2$.

In this process, the quantity used of the reagent of formula $Cat^+X^-$ may be such that about 4 moles of RX are used per mole of reagent, and suitably there is used at least one mole of reagent per 5 moles of RX. As stated, the molar ratio of reagent:RX may be 1:5 and the reaction products will still contain, on a molar basis, a triorganotin halide of the formula $R_3SnX$ as the predominant product of general formula $R_aSnX_{(4-a)}$.

The quantity of tin put into the process may be considerably more than the small excess over the 2 moles per mole of reagent shown above, for the extra tin simply remains unreacted and can be recycled. In fact, a convenient method of operating is to add most of the tin that will theoretically be needed at the start of the reaction, and then as the reaction proceeds, add more tin in amounts that need not be exactly controlled, so that some unreacted tin is always available.

To ensure that the compound of formula $Cat^+X^-$ is present in reagent amount and even in molar excess over the organic halide, it is convenient to add the organic halide to a reaction mixture containing tin and the compound. As the reaction proceeds more organic halide is slowly added, and the reagent is consumed in forming the products indicated by the above equation, until the production of triorganotin halides substantially ceases. A by-product is also formed. This is a halogenotin complex containing $Cat^+$, tin and halogen (X) which can be chlorine, bromine or iodine or a mixture of all three.

The tin can be in its 2 or 4, and possibly in its 3, valence state. Generally, therefore, the halogenotin complex may have an empirical formula:

$$Cat_dSn_eX_f$$

where
d is 1 or 2
e is 1 or 2
f is 3 to 6

However, since these complexes are the by-products from the preparation of organotins, these organotins and partially substituted tins may also be present such as for example $Bu_4N^+BuSnBr_4^-$, $Oct_4N^+Bu_2SnBr_3^-$ (Oct=octyl), etc.

Further, since the tin (2) species can absorb oxygen, oxygen compounds may also be present.

When the quantity of the reagent is less, relative to the organic halide, than that needed for production of triorganotin halides, the reaction can be stopped, e.g., by distilling out the unused organic halide.

In our process where the compound of formula $Cat^+X^-$ is used in reagent amount, there is formed a substantial amount of a halogenotin complex by-product mixture containing tin in combined form, in such quantity that it is economic to treat the by-product to recover the tin and the reagent compound in a form in which they can be re-used in the production of organotin halides. Whatever the halogenotin complexes are, the method of treatment of them, which is a further feature of the present invention, makes it possible to recover from it the tin and reagent compound in re-usable form. If desired, halide may also be recovered from the by-product as metal halide which can be converted to organic halide for re-use in the process of the invention.

In brief, the by-product, which is insoluble in water, is separated from the desired product, which latter is a mixture of organotin halides, and is subjected to electrolysis.

The method for such electrolysis provided by this uses a two-phase electrolyte system in which the catholyte is the water-insoluble by-product and the anolyte is an aqueous electrolyte. The anode, immersed in the aqueous electrolyte, may be a non-corrodible anode such as platinum or graphite, in which case tin metal is recoverable from the by-product and deposited on the cathode. Alternatively, the anode may be a non-corrodible anode such as stainless steel or nickel placed in an aqueous alkali metal hydroxide anolyte which is separated in turn by a cation exchange membrane from an intermediate electrolyte of aqueous alkali metal halide, e.g., sodium bromide. When this three-phase electrolyte system is used, tin metal from the by-product is deposited on the cathode and in addition more alkali metal halide is formed in the intermediate electrolyte (with alkali metal ion from the anolyte and halide ion from the by-product) and can be recovered for further use. If a separate tin anode, placed in the aqueous alkali metal halide, is also used in addition to the non-corrodible anode, a product enriched in tin and ready for reuse is obtained.

The electrolysis process may be represented thus:

$$Bu_4NSnBr_3 \rightarrow Bu_4NBr + 2Br^- + Sn°$$

or $$(Bu_4N)_2Sn_2Br_6 \rightarrow Bu_4NBr + 2Br^- + Sn° + Bu_4NSnBr_3$$

The product of our above-described process is a mixture of organotin halide product and the by product and this mixture can be treated with a solvent, preferably a hydrocarbon solvent, to remove the organotin halides in solution and leave the insoluble by-product which can then be treated electrolytically for recycle as described above.

The organotin halides are, in the usual form of our process, a mixture of a major amount of triorganotin halides and a minor amount of diorganotin halides with perhaps other organotins. The minor amount of di- and monoorganotin halides can be removed from this mixture by treatment with an aqueous phase of the reagent compound of the formula $Cat^+X^-$, (or the pure liquid compound) e.g., tetrabutylammonium bromide, which reacts with mono- and diorganotin halides to form complex halostannites and which can thus be extracted from the organo solution of the triorganotin halides which can in turn be recovered from the solution by distillation.

The complex halostannite (formed by reaction of diorganotin halide with the reagent) may have, for example, the formula $Cat^+R_2SnX_3^-$; this formula is, however, suppositional. However, such complex can be reacted with tin and RX to form $R_3SnX$ and $Cat^+SnX_3^-$ which are then separated for recovery of the triorganotin halide and electrolysis of the complex. Thus the further treatment of the complex halostannite is itself a process according to the invention.

Furthermore, it is possible to use a mono- and/or diorganotin halide as a starting material by the process of this invention; if it is included in the initial mixture of tin and $Cat^+X^-$, it reacts with the $Cat^+X^-$ to form the complex halostannite which then reacts further with the other reagents when RX is added to the mixture. The mono- and/or diorganotin halide used as starting material need not itself have been made by the process of this invention (an example of this procedure is in Example 9 below).

The final triorganotin halide product obtained by this process may be hydrolysed, e.g., with NaOH, to form triorganotin oxide (e.g., bis(tributyltin oxide, TBTO) which is withdrawn as product leaving a halogen salt, e.g., NaBr. The halogen salt can be reacted with an alcohol in the presence of an acid to form organic halide which can be for re-use as feed to the process. Example 10 below illustrates a cyclic process according to this invention in which the only feeds are tin and an alcohol to supply the organo groups, (plus alkali metal hydroxide and acid), all other materials being recycled by the electrolysis procedures.

The tin supplied to our process may be elemental tin, in any of the forms previously used for making organotin halides such as sheet metal, metal powder, or granulated tin, or a tin alloy, especially an alloy with a metal present as a galvanic catalyst. However, the preferred source of tin in the process of the invention is elemental tin in the form of dendrites.

Tin may be produced in the form of dendrites by an electrolytic process similar to that described above for the treatment of by-product. An electric current is passed between a tin anode and an inert, e.g., stainless steel, cathode, through an electrolyte system having an aqueous, e.g., alkali metal halide, anolyte and a water-immiscible catholyte which is suitably a water-insoluble tin salt, e.g., the halogenotin complex as described above. Dendritic tin is deposited on the cathode.

The organic groups R in our organotin halide product need not be all the same; for example, we may form a dibutyloctyltin halide or a methyldibutyltin halide. Thus, the organic halide RX may be a mixture of halides, for example butyl halide and octyl halide. The organic group R in the product may also be provided by the above-described reagent of the formula $R_2QX$ and R in that reagent need not be the same organic group as R in the organic halide. Similarly X in the reagent $Cat^+X^-$ need not be the same halogen as in the organic halide RX. The organic groups R are preferably aklyl groups, n-butyl being especially preferred.

EXAMPLES OF THE INVENTION

The invention will now be described in detail in some examples (all temperatures are in degrees Centigrade):

EXAMPLE 1

Production of tributyltin bromide

Two moles of tetrabutylammonium bromide are melted (temperature in excess of 105°) and dendritic tin is stirred into the melt—a total of 6.6 moles of tin is added in the course of the reaction and the greater part of this, above 5 moles, is added at the start of the reaction. When the initial tin has been added, the temperature is raised to above 120° and kept in the range 120°–140° throughout the reaction. Butyl bromide is added to the mixture at a constant rate, sufficient to provide a total of 8 moles butyl bromide in the course of three hours. At the end of three hours the reaction vessel is maintained at 120°–140° for one further hour without addition of any further butyl bromide and then is cooled. A liquid is decanted from residual tin in the vessel and extracted with a hydrocarbon solvent of b.p. 145°–160° to recover the desired product. After separation from the solvent, there are recovered 844 g of product of which 700 g is tributyltin bromide and 140 g is dibutyltin dibromide.

EXAMPLE 2

Preparation of Triorganotin Compounds

Dendritic tin was prepared by the electrolysis of an aqueous solution of sodium bromide (10–15%) containing $SnBr_2$ (10–20 g/l Sn) in a 25 liter polypropylene tank using a tin anode and a stainless steel rod as cathode (area about 40 cm²). This cell was operated at 50°–70° and 30 to 100 Amps. The dendritic tin was removed periodically from the cathode and the cell, washed and dried. The dried product (a fluffy interlocked mass of dendrites) had a low bulk density—between 0.2 and 0.5 g per cc.

Dendritic tin produced in this way was reacted with tetrabutylammonium bromide ($Bu_4NBr$) and butyl bromide (BuBr) in a 2 liter round-bottom flask fitted with a condenser, thermometer, and dropping funnel with its outlet extended below the level of the reaction mass in the flask.

The $Bu_4NBr$ and some of the dendritic tin (usually about 50% of the charge) were loaded into the flask and heat applied to melt the $Bu_4NBr$ and maintain the temperature throughout the reaction. Butyl bromide was added from the dropping funnel at such a rate as to maintain the reaction temperature, and as the dendritic tin was consumed the rest of the tin was added.

This reaction was effected 17 times using different amounts of the reagents or different reaction conditions each time.

The quantities involved and the reaction conditions are set out for each of the 17 experiments in the following Table 1.

At the end of the reaction the flask contained a liquid mixture of reaction products and residual tin, and the liquid mixture was decanted off the tin. This liquid mixture was extracted with hydrocarbon (b.p. 145°–160°) at 80° three times using the same volume of hydrocarbon as of the liquid mixture each time. The residue, insoluble in hydrocarbon, was a yellow-khaki water-insoluble by-product, which can be treated electrolytically for the recovery of tin and nucleophile generator. The three hydrocarbon extracts were distilled to remove hydrocarbon and leave a product mixture containing dibutyltin dibromide ($Bu_2SnBr_2$) and tributyltin bromide ($Bu_3SnBr$) in the amounts shown in the table.

TABLE I

| Ex. No. | Starting Reagents | | | Add'n. times Hours | React'n. times Hours | React'n. temp. °C. | Recovered Products | | | | |
|---|---|---|---|---|---|---|---|---|---|---|---|
| | Tin Moles | Bu$_4$NBr Moles | BuBr Moles | | | | Tin Moles | BuBr Moles | by-product g | Bu$_3$SnBr Moles | Bu$_2$SnBr$_2$ Moles |
| 1 | 4.0 | 2.0 | 6.0 | 4 | 2 | 140 | 0.67 | 0.26 | 1439 | 1.23 | nil |
| 2 | 6.7 | 2.0 | 8.0 | 4 | 2 | 140 | 3.37 | 0.07 | 1348 | 2.15 | 0.31 |
| 3 | 6.7 | 2.0 | 8.0 | 4 | 2 | 140 | 1.9 | 0.09 | 1379 | 1.82 | 0.44 |
| 4 | 6.7 | 2.0 | 8.0 | 3 | 3 | 140 | 2.66 | 0.79 | 1253 | 1.70 | 0.41 |
| 5 | 6.7 | 2.0 | 8.0 | 5 | 4 | 120 | 3.08 | 1.21 | 1303 | 1.47 | 0.26 |
| 6 | 6.7 | 2.0 | 8.0 | 4.5 | 10 | 115–120 | 3.9 | 0.28 | 1281 | 1.37 | 0.48 |
| 7 | 6.7 | 2.0 | 8.0 | 3 | 3.5 | 140 | 2.0 | 0.11 | 1426 | 1.60 | 0.46 |
| 8 | 4.0 | 2.0 | 6.0 | 4 | 2 | 135–160 | 1.01 | 1.07 | 1342 | 0.78 | nil |
| 9 | 4.0 | 2.0 | 6.0 | 4 | 2 | 140–150 | 0.66 | 0.55 | 1291 | 1.31 | 0.07 |
| 10 | 5.0 | 2.0 | 6.0 | 4 | 2 | 145–160 | 1.61 | 0.24 | 1254 | 1.33 | nil |
| 11 | 5.0 | 2.0 | 6.0 | 4 | 2 | 130–135 | 3.06 | 0.64 | 1185 | 0.94 | nil |
| 12 | 4.0 | 2.0 | 6.0 | 4 | 2 | 120–125 | 1.47 | 1.50 | 1236 | 0.72 | nil |
| 13 | 4.0 | 2.0 | 6.0 | 4 | 6 | 120–130 | 1.23 | 0.48 | 1159 | 1.08 | nil |
| 14 | 4.0 | 2.0 | 7.0 | 4 | 4 | 120 | 1.45 | 1.64 | 1184 | 0.99 | nil |
| 15 | 4.0 | 2.0 | 8.0 | 4 | 4 | 120 | 0.95 | 2.9 | 1312 | 0.94 | nil |
| 16 | 5.0 | 2.0 | 8.0 | 4 | 4 | 120 | 1.90 | 2.6 | 1303 | 1.19 | nil |
| 17 | 6.0 | 2.0 | 8.0 | 4 | 4 | 120 | 2.3 | 1.19 | 1303 | 1.37 | nil |

EXAMPLE 3

The reactor was a 10 liter round-bottom flask fitted with an anchor stirrer, thermometer, condenser, and dropping funnel.

Tetrabutylammonium bromide (1610 g, 5 moles) and dendritic tin, as used in example 2 (1500 g. 12.6 moles), were loaded into the reactor and heated to 130°. Butyl bromide (2740 g, 20 moles) was added dropwise with slow stirring (25 r.p.m.) such that the reactor temperature remained at 130° (4 hours). The reaction mixture was then maintained at 130° for a further 8 hours, and after which the excess BuBr was removed under vacuum (about 200 g).

The reaction product was extracted with a hydrocarbon (b.p., 145°–160°, 3×3 liters) leaving a yellow-khaki by-product residue (3750 g) containing some residual tin. The combined hydrocarbon extracts were distilled to give 2088 g of product (b.p. 150°/10 mm) which was found on analysis by gas liquid chromatography (GLC) to contain 90% Bu$_3$SnBr and 10% Bu$_2$SnBr$_2$.

EXAMPLE 4

Example 3 was repeated but the reaction temperature was maintained at 110°. This gave a residue after extraction (3895 g) containing more residual tin than example 3 and less distilled product (1550 g) which analysed at 90% Bu$_3$SnBr and 10% Bu$_2$SnBr$_2$.

EXAMPLE 5

(Electrolysis and tin-enrichment of by-product, followed by conversion of tin-rich product of electrolysis to triorganotin halides.)

For the electrolysis of by-product there was used the double-anode cell illustrated in schematic section in FIG. I of the accompanying drawings. This cell comprises a polypropylene tank 10 (40 cm×40 cm×25 cm) containing a stainless steel cathode 11, 35 cm×25 cm×0.3 cm, connected to an insulated conductor 12. The cell was charged with a volume of 9.83 kg of the hydrocarbon-insoluble yellow-khaki by-product obtained in Examples 2 and 3 (a mixture of the results from the 18 experiments) to cover the floor of the cell, as shown at 13. The by-product contained about 5% of the hydrocarbon (b.p. 145°–160°) used to extract the organotin products, and about 2% free Bu$_4$NBr.

Above the by-product layer 13 was placed 16 l of 20% aqueous NaBr solution, reference number 14, as intermediate electrolyte. Extending into the intermediate electrolyte 14 was an anode chamber 15 with an ion-exchange membrane wall (Nafion TM, available from du Pont) and containing as anolyte a solution 16 of 20% NaOH into which a nickel anode 17 extended. Extending into the intermediate electrolyte 14 was a tin anode 18 (weight 9.97 kg) held on a feeder 19. The anodes 17 and 18 were connected to the positive terminal of a variable power source of DC (not shown) and the cathode conductor 12 to the negative terminal.

A current of approximately 100 amps was then passed through the cell over a period of about 11 hours. During this time the cell voltage fell from an initial 20 V to a final value of 5 V and the cell temperature varied between 50° and 100°. The current carried by each anode was monitored and adjustments made (by disconnecting one or other anode) so that each anode carried approximately the same total number of amp-hrs.

At the end of the electrolysis the nickel anode had passed 550 amp-hrs evolving oxygen, and the tin anode had passed 530 amp-hrs, losing 1.1 kg of tin. Sodium bromide was formed in the intermediate electrolyte 14 and fine dendritic tin and Bu$_4$NBr were formed at the cathode 11. About 680 g of Bu$_4$NBr appeared in the electrolyte 14.

The final catholyte was a blackish, lumpy, mobile fluid (8.52 kg) which contained 9% water, about 25% Bu$_4$NBr, about 25% dendritic tin and about 41% unreacted by-product.

Some of this final catholyte (6.17 kg, as much as the next container could conveniently hold) was transferred to the reactor described in Example 3 and heated under vacuum to remove water. Over the course of four hours butyl bromide was added to the electrolysis product (which contained about 1540 g, i.e., 13 moles of tin and 1550 g, i.e, 4.8 moles, of Bu$_4$NBr) through a funnel dipping below the surface of the reaction mass at such a rate that the temperature in the reactor stayed around 140°; at the end of four hours, 2466 g (18 moles) of BuBr had been added. The reaction mix was then maintained at 140° for a further eight hours. Excess BuBr was then distilled off (363 g) and the residue was cooled and extracted with hydrocarbon solvent (b.p. 145°–160°, using 3 l of solvent on each of 3 extractions), leaving a yellow-khaki residue, (5.4 kg), containing some tin dendrites. The hydrocarbon extracts were combined and distilled yielding a product of b.p. 150°/10 mm. This product weighed 1894 g and contained 87% Bu$_3$SnBr (4.46 moles) and 12% Bu$_2$SnBr$_2$ (0.57 mole).

EXAMPLE 6

Electrolysis of by-product and recycle of the electrolytic products

Some of the water-insoluble yellow-khaki by-product obtained in Example 2 was subjected to electrolysis in the apparatus shown in FIG. II of the accompanying drawings; the material used was a mixture of that obtained from all 17 experiments.

This cell shown in FIG. II comprises a polypropylene tank 20, 30 cm diameter, 40 cm high containing a stainless steel cathode 21, 15 cm×20 cm×0.16 cm connected to an insulated feeder 22. The anode 23 is a cylinder of tin (approx. 8 cm diameter and 17 cm long) weighing about 6 kg.

This cell was loaded with a lower layer of 6 kg of the by-product 24 from the production of tributyltin bromide.

Seven liters of 20% aqueous NaBr solution was added as the anolyte layer 25. The anode 23 was connected to the positive terminal of a DC power supply, the cathode 21 to the negative and a current of 50 to 60 amps was passed until a total of 360 amp-hrs had been passed. The starting voltage was 20 volts, starting temperature 80°; at the end these were respectively 8 volts and 60°.

At the end of this electrolysis the tin anode 23 had lost 770 g in weight, and 770 g of fine dendritic tin had been formed at the cathode 21.

The tin anode 23 was then removed and the anode compartment 30, shown in FIG. III, installed. The anode compartment 30 is a polypropylene tube 30, 10 cm diameter, with an ion exchange membrane 32 sealing the bottom. The anode therein is a stainless steel tube 33. Compartment 30 was partially filled with 25% sodium hydroxide as anolyte 34. This cell was then connected in the usual way to the DC power supply and a current of 50-70 amps passed until 288 amp-hrs had been passed.

Oxygen was evolved at the anode, sodium bromide formed in the aqueous intermediate layer and tin dendrites and Bu$_4$NBr were formed in the catholyte 24.

The catholyte (5.07 kg) contained 2.18 kg unreacted halogenotin complex by-product, Bu$_4$NBr (1.18 kg), dendritic tin (1.4 kg), and water (0.3 kg).

The product of this two-phase electrolysis, containing approximately 10% water, 25% fine dendritic tin, 25% Bu$_4$NBr (3.9 mole) and 40% unreacted by-product, was heated in the reactor described in Example 3 to remove the water.

Butyl bromide (2330 g, 17 moles) was added over 7 hours with stirring such that the reaction temperature was maintained at 150°. The reaction mixture was cooled and extracted with hydrocarbon (b.p., 145°-160°, 3×3 liters) at 80°, leaving a yellow-khaki residue containing some tin. The hydrocarbon extracts were distilled giving 1663 g of product, b.p. 150°/10 mm which analysed as about 80% Bu$_3$SnBr and 20% Bu$_2$SnBr$_2$.

EXAMPLE 7

The starting materials shown in Table 2 were weighed into a 500 ml conical flask containing a PTFE-coated magnetic follower. A condenser was fitted and the flask heated and stirred on a magnetic hot plate for 16 hours at 100°-120°. Then the liquid phase was separated from the remaining tin and analysed for butyl tins by GLC.

The experimental data and results are given in table 2; the tin powder was −300 mesh; Et$_4$NI is tetraethyl ammonium iodide; DMF is dimethyl formamide; diglyme is diethyleneglycol dimethyl ether; Bu$_2$O is dibutyl ether.

TABLE II

| Exp. No. | Starting materials (Moles) | | | Nucleophile generator | Solvent (g) | Products (Moles) | | Mole Ratio Bu$_3$/Bu$_2$ |
|---|---|---|---|---|---|---|---|---|
| | Tin Powder | Butyl Bromide | Iodine | | | Bu$_2$SnBr$_2$ | Bu$_3$SnBr | |
| 1 | 0.5 | 0.5 | 0.01 | Et$_4$NI 0.05 | DMF 50 | 0.009 | 0.069 | 7.56 |
| 2 | 0.2 | 0.3 | 0.01 | Bu$_4$NI 0.05 | dibutyl ether | 0.018 | 0.037 | 2.1 |
| 3 | 0.5 | 0.57 | 0.01 | Et$_4$NBr 0.05 | — | 0.011 | 0.03 | 2.6 |
| 4 | 0.5 | 0.3 | — | KBr 0.25 CuBr 0.05 | diglyme 50 | 0.006 | 0.009 | 1.5 |
| 5 | 0.5 | 1.0 | 0.01 | NaSnBr$_3$ 0.1 | diglyme 50 | 0.149 | 0.158 | 1.07 |
| 6 | 1.0 | 0.5 | — | Bu$_4$NBr 0.1 | white spirit 50 | 0.022 | 0.10 | 4.6 |
| 7 | 1.0 | 1.0 | — | Bu$_4$NBr 0.1 | white spirit 50 | 0.033 | 0.102 | 3.0 |
| 8 | 1.0 | 1.5 | — | Bu$_4$NBr 0.1 | white spirit 50 | 0.032 | 0.089 | 2.8 |

EXAMPLE 8

Purification of Organotin Product

The starting material for this experiment was a mixture of dibutyltin dibromide (222 g, 0.56 mole) and tributyltin monobromide (885 g, 2.4 mole) obtained in the previous experiments on the direct reaction to produce triorganotins, and separated from the yellowish residue by solvent extraction. The mixture was heated with tetrabutylammonium bromide (200 g, 0.62 mole) at 80° for about 15 minutes with stirring. A sample of the supernatant liquor was analyzed by GLC and indicated a Bu$_3$SnBr content of at least 95% and a Bu$_2$SnBr$_2$ content less than 5%; evidently most of the diorganotin dihalide had become complexed.

The total mixture was then extracted with hydrocarbon (b.p. 145–160) 3 times using one liter each time, leaving a residue of $Bu_2SnBr_2$—$Bu_4NBr$ complex (432 g, 102% yield). The combined hydrocarbon extracts were distilled leaving a residual oil (895 g, 101% yield) which analyzed by GLC as $Bu_3SnBr$ free of $Bu_2SnBr_2$.

This experiment was repeated giving a $Bu_2SnBr_2$—$Bu_4NBr$ residue (428 g) and hydrocarbon-soluble oil (933 g) which on analysis by GLC was $Bu_3SnBr$ free of $Bu_2SnBr_2$.

Thus this invention also provides, as a separate matter, a method of separating triorganotin halides from other organotin halides in a mixture thereof, which comprises reacting the mixture with a compound of formula $Cat^+X^-$ as defined above thereby forming a hydrocarbon-insoluble complex of the components other than triorganotin, and then subjecting the mixture to solvent extraction with a liquid which is a solvent for the triorganotin halides and a nonsolvent for the complex.

EXAMPLE 9

Use of Diorganotin Dihalide as a Starting Material

A mixture of $Bu_2SnBr_2$ (409 g, 1.04 mole) and $Bu_3SnBr$ (83 g, 0.22 mole) was contacted with $Bu_4NBr$ (322 g, 1 mole) and allowed to complex therewith, and the complex was mixed with granulate tin (237 g, 2 mole). Butyl bromide (137 g, 1 mole) was poured into the mixture, and the reaction mass held at 140° for 2 hours.

The liquor was decanted from the residual tin which was then washed with hydrocarbon (500 ml) and this washing combined with the decanted liquor. The washed residual tin amounted to 110 g (0.93 mole). The mixture of decanted liquor and hydrocarbon washings separated into two phases, which were then separated. The bottom phase was extracted with more hydrocarbon (500 ml, then 1 liter) leaving a residue of halogenotin complex (678 g, 1.1 mole), the combined hydrocarbon extracts were distilled leaving an oil (465 g) which analysed by GLC as $Bu_3SnBr$ (394 g, 1.06 mole) and $Bu_2SnBr_2$ (71 g, 0.18 mole).

EXAMPLE 10 (Cyclic process)

As mentioned above, by the use of the various recycling steps which have been described, it is possible to arrange this process as a cyclic process whereby triorganotin compounds can be produced directly from tin and cheap starting materials such as alcohols, alkali and mineral acid. For example, the commercially valuable bis(tributyltin)oxide (TBTO) can be produced from tin, butanol, sodium hydroxide and sulphuric acid. The more expensive halogen used in producing triorganotin halide is recovered and recycled, and the $Cat^+X^-$, e.g., tetrabutylammonium bromide, is similarly recycled. The organization of this process as a cyclic process, which can even be continuous, is shown diagrammatically in FIG. 5 of the accompanying drawings.

For the case where $Cat^+X^-$ is $(n\text{-Butyl})_4N^+Br^-$ the equations for the preparation of TBTO are:

$$3BuOH + 3NaBr + 1.5H_2SO_4 \rightarrow 3BuBr + 3H_2O + 1.5Na_2SO_4 \quad (1)$$

$$3BuBr + 2Sn + Bu_4NBr \rightarrow Bu_3SnBr + Bu_4N^+SnBr_3^- \quad (2)$$

$$Bu_3SnBr + NaOH \rightarrow 0.5(Bu_3Sn)_2O + NaBr + 0.5H_2O \quad (3)$$

$$Bu_4NSnBr_3 + 2NaOH + Sn(\text{Massive}) + 4 \text{ Faradays} \rightarrow Bu_4N^+Br^- + 2Sn(\text{dendritic}) + 2NaBr + H_2O + 0.5O_2 \quad (4)$$

Thus the overall process may be represented by:

$$3BuOH + Sn + 3NaOH + 1.5H_2SO_4 + 4 \text{ Faradays} \rightarrow 0.5(Bu_3Sn)_2O + 1.5Na_2SO_4 + 0.5O_2 + 4.5H_2O$$

This is shown in the following example, which is also illustrated in FIG. V.

Sodium bromide produced in an electrolytic cell in a similar manner to that described in example 6 and sodium bromide from the hydrolysis of tributyltin bromide described below can be combined and reacted with sulphuric acid and butanol by heating under reflux to produce butyl bromide which can be recovered by distillation.

Cell product, similar to that produced in Examples 5 and 6, containing approximately 25% dendritic tin, 25% tetrabutylammonium bromide, and 50% unreacted by-product (after dehydration), can be reacted with the butyl bromide from above in a similar manner to that described in Examples 5 and 6, producing after extractive separation, a yellow-khaki by-product and a hydrocarbon extract containing mainly tributyltin bromide with some dibutyltin dibromide.

The yellow-khaki by-product can be electrolysed in a similar manner to that described in Examples 5 and 6, to produce a cell product containing dendritic tin, tetrabutylammonium bromide and unreacted by-products, as well as aqueous sodium bromide.

The hydrocarbon extract solution of mainly tributyltin bromide with some dibutyltin dibromide can be purified using tetrabutylammonium bromide in a similar manner to that described in Example 8, leaving a solution of tributyltin bromide in hydrocarbon. This can then be agitated with aqueous sodium hydroxide to give a hydrocarbon solution of bis(tributyltin)oxide and an aqueous solution of sodium bromide. The aqueous solution, after separation, can be used for butyl bromide preparation. The hydrocarbon solution itself can be distilled to give TBTO.

EXAMPLE 11

Crude tributyltin bromide ($Bu_3SnBr$) containing up to 28% dibutyltin dibromide ($Bu_2SnBr_2$), and halogenotin by-product were prepared in a series of experiments, A–G. These involved heating tributylamine ($Bu_3N$) with excess elemental tin and adding butyl bromide (BuBr) at a rate such that the reaction temperature of 130°–140°. was maintained. When this addition was complete, the reaction mass was maintained at 130°–140° for several hours more. Excess BuBr was then removed by distillation. After cooling to about 60°–80° the reaction liquor was decanted from the unreacted tin and extracted with 3 volumes of hydrocarbon spirits (b.p 145°–160°). The extracts were combined and the hydrocarbon distilled off leaving the crude $Bu_3SnBr$-$Bu_2SnBr_2$ mixture. The halogenotin complex by-product remaining after the extraction was heated under vacuum to remove any residual hydrocarbon extractment and the product stored in plastic containers. The amounts of materials used and the products obtained are shown in table III.

EXAMPLE 12

The halogenotin complex by-product from the experiments of example 11 was electrolysed in a laboratory cell, as illustrated in section in FIG. IV. This cell has a polypropylene body 41 with a cross section of approximately 30 cms×30 cms and an overall height of approximately 45 cms. The cell has a polypropylene bottom valve 42 and is mounted on feet (not shown) so that the bottom inverted-pyramidal part fits through a hole in the bench. The cell is heated by external electrical heating tapes 43 and is insulated and clad 44. The cell has two further drain taps 45 and 46 in its higher portion.

Internally the cell has two cathode plates 47 connected to cathode current feeders 56. Above the cathodes there are two tin anodes 48, (one only shown) mounted on mild steel current feeders 58 which in turn are supported on insulated bushes on an anode support frame 49 which is screwed to the bench. Alongside the tin anodes in a third anode 50 made of nickel. This nickel anode is supported on a mild steel feeder 57 and held from the anode support frame 49. The nickel anode 50 is separated from the rest of the cell inside a compartment made up from outer clamping members 51, an inner member 52 and two ion exchange membranes 53. Parts 51 and 52 are U-shaped in section and are clamped together with bolts sandwiching the membranes 53 so that a five-sided compartment with an open top is formed.

TABLE III

| Exp. No. | Starting Materials | | | | Products $Bu_3SnBr$ - $Bu_2SnBr_2$ | | | Halogenotin Complex By-product Kg |
|---|---|---|---|---|---|---|---|---|
| | $Bu_3N$ Kg | Tin Kg | BuBr Kg | Tin* Kg | Weight Kg | % $Bu_3SnBr$ | % $Bu_2SnBr_2$ | |
| A | 1.85 | 2.37 | 5.56 | Trace | 2.87 | 89 | NA | 6.4 |
| B | 2.17 | 2.78 | 6.89 | — | 2.92 | 70 | 28 | 7.75 |
| C | 1.88 | 2.41 | 5.98 | — | 2.87 | NA | NA | 5.81 |
| D | 1.29 | 1.8 | 4.15 | 0.1 | 2.41 | 73 | 21 | 4.37 |
| E | 1.85 | 2.37 | 5.9 | 0.23 | 2.85 | 74 | 26 | 6.2 |
| F | 1.85 | 1.58 | 4.41 | 0.06 | 1.11 | NA | NA | 5.95 |
| G | 1.85 | 1.58 | 4.41 | 0.5 | 1.1 | NA | NA | 7.2 |

\* = Residual elemental tin
NA = Not Analyzed

The cell has two polypropylene scrapers 54 with blades 54a which can be pushed across the top of the cathodes 47 to dislodge metal formed on the cathodes and to push this metal into the bottom part of the cell (i.e., below the cathodes). The cell has an agitator on a revolving shaft 55 connected to a motor (not shown). This agitator is used to stir the bottom phase containing the metal particles.

In operation the tin anode feeders 58 and the right-hand cathode feeder 56 are connected to one rectifier (not shown), and the nickel anode feeder 57 and the left-hand cathode feeder are connected to another rectifier. The tin anodes can be adjusted in height up and down on their feeders 58.

The cell was loaded with 25.9 kg of mixed halogenotin complex by-product from example 11, and 16 liters of 10% wt/volume sodium bromide solution. This resulted in a two-phase system with the halogenotin complex below the aqueous solution, and with the interface therebetween about 1 cm above the cathode plates 47. Two liters of 25% aqueous sodium hydroxide were poured into the anode compartment formed by 51, 52 and 53. The cell contents were then heated to 75°–95° and current passed from both rectifiers. A total of 1103 amp-hrs was passed through the nickel anode and 1163 amp-hrs through the tin anodes.

The electrolysis products were 17.7 liters of 30% wt/volume sodium bromide solution and 24 kg of a mixture of $Bu_4NBr$-dendritic tin-halogenotin by-product. The tin anodes had lost a total of 2.57 kg of tin. About 1 kg of the bottom phase was removed and a further 4 kg of by-product from Example 11 added. Most of the aqueous phase was removed via tap 45 and water added to the remainder to dilute the sodium bromide solution to approximately 10%. A further 924 amp-hrs were passed through the tin anodes, resulting in a loss of 1.89 kg therefrom, while a further 844 amp-hrs were passed through the nickel anode.

The bottom phase was then run off through valve 42 and analysed. Analysis indicated that this phase contained 23.4% dendritic tin and 28% $Bu_4NBr$ and about 1% water; its total weight was 26.5 kg. 9.3 kg of this material was heated under vacuum to remove the water and a total of 4.3 kg butyl bromide added while heating between 100° and 150°. The excess butyl bromide was then distilled and the reaction mass extracted with hydrocarbon spirits (b.p. 145°–160°). Distillation of the hydrocarbon extracts gave a crude product (2.79 kg), analysing as 86% $Bu_3SnBr$ and 14% $Bu_2SnBr_2$. The residue after extraction was composed of halogenotin complex (8.3 kg) and dendritic tin metal (0.9 kg)

EXAMPLE 13

The cell described in example 12 was loaded with 14.3 kg of the bottom phase from example 12, 10.6 kg of the combined halogenotin complex by-products from example 11 and 16 liters of 9.5% sodium bromide solution. 2.5 liters of 25% sodium hydroxide was loaded into the membraned nickel anode compartment. A total of 342 amp-hrs were passed through the tin anodes and 452 amp-hrs through the nickel anode.

The bottom phase (23 kg) was run off and treated in two portions to remove water (625 g) and reacted with butyl bromide (total 5.36 kg) at 110° to 150°. The excess butyl bromide was distilled under vacuum and the residue extracted with hydrocarbon. The hydrocarbon extracts were distilled leaving a residue of crude $Bu_3SnBr$ (total 2.0 kg) which, analysed by GLC, was mainly $Bu_3SnBr$. The total residue after extraction amounted to 18.8 kg and about 1 kg of unreacted tin metal.

EXAMPLE 14

The halogenotin and butyltin halogeno complex residues from examples 11, 12 and 13 were now combined and loaded into the cell as described in example 12 with 16 liters of 8% sodium bromide solution as the upper phase. 2 liters of 25% aqueous sodium hydroxide was loaded into the nickel anode compartment. This three electrolyte system was then electrolysed at 75°–100°, with a combined current of about 100 amps at a voltage of 10–20 volts. A total of 1181 amp-hrs were passed through the tin anodes and 1180 amp-hrs through the nickel anode. The bottom phase was analysed and found to contain approximately 10% dendritic tin, 20% Bu$_4$NBr and 4% water.

About 20 kg of this bottom layer were converted to butylated tin products in three portions by removing the water under vacuum, adding butyl bromide at 150°–155° over 5–6 hours, removing the excess butyl bromide under vacuum, extracting the organotin with three volumes of hydrocarbon and distilling the extracts. The extraction leaves the halogenotin complex as an insoluble residue. The details are given in Table IV.

EXAMPLE 15

Tributylamine (18.5 kg, 100 mole) butyl bromide (54.8 kg, 400 mole), and granulated tin (23.75 kg, 200 mole) were heated in a glass lined 250 liter capacity steam heated vessel to 125°–150° C. for 24 hours under nitrogen. More tributylamine (37 kg, 200 mole) and granulated tin (73.5 kg, 620 mole) were added and the resulting mixture heated to 125°–150°, butyl bromide (110 kg., 800 mole) was added over 4 hours and the mixture heated for a further 6 hours. The reaction mass was cooled and a sample analysed by extracting with three volumes of hydrocarbon; the hydrocarbon soluble portion was distilled to remove the hydrocarbon, leaving 13.2% by weight which analysed by GLC as 97.5% Bu$_3$SnBr and 2.5% Bu$_2$SnBr$_2$. The hydrocarbon insoluble portion was 69% by weight and contained 20.2% tin.

More granulated tin (26 kg., 219 mole) was added and the resulting mixture heated to 125°–150° for a further 4 hours. The reaction mass was cooled and sampled and analysed as before. The organotin fraction was 34.9% by weight of the sample analyzing as 97% Bu$_3$SnBr and 3% Bu$_2$SnBr$_2$, and the hydrocarbon insoluble portion was 61.6% by weight and contained 21.3% tin. The sample of reaction mixture when first taken was nearly white.

drocarbon insoluble residue (281 g) which analysed at 23.3% tin, 12.1% bromine and 12.6% chlorine. The hydrocarbon extracts were combined and the hydrocarbon distilled leaving an organotin residue (51 g).

The organotin product was shown by GLC to be a mixture of mainly Bu$_3$SnCl and Bu$_3$SnBr. It analysed at 38% tin, 7.3% bromine and 7.4% chlorine. The calculated values for a mixture of 66% Bu$_3$SnCl and 34% Bu$_3$SnBr are 36% tin, 7.3% bromine and 7.2% chlorine.

EXAMPLE 17

Granulated tin (43 g, 0.36 mole) and Bu$_4$NBr (58.4 g, 0.18 mole) were heated to 140°–150° in a flask fitted with a condenser thermometer and dropping funnel. Butyl iodide (100 g, 0.54 mole) was added over 2.5 hours keeping the temperature at 140°–150°. The reaction mass was heated for a further 16 hours. After this time the reaction mass weighed 196.8 g. The liquor was decanted from the unreacted tin and the tin washed with acetone and dried, leaving a residue of 5.7 g of tin. The decanted liquor (185 g) was extracted with hydrocarbon (b.p. 145°–160°, 2×200 ml) leaving a hydrocarbon insoluble residue (124 g) which analysed at 16.8% tin, 29.6% iodine and 7.9% bromine. The hydrocarbon extracts were combined and the hydrocarbon distilled leaving an organotin residue (56.8 g). This organotin product was shown by thin layer chromatography (TLC) to be a mixture and analysed at 31% tin, 26% iodine and 5.6% bromine. The calculated values for Bu$_3$SnI are 28.5% tin and 30.4% iodine.

EXAMPLE 18

Granulated tin (118.7 g, 1 mole) and Bu$_4$NBr (161 g, 0.5 mole) were heated to 140°–150° in a flask fitted with a condenser, thermometer and dropping funnel. Octyl bromide (289.6 g, 1.5 mole) was added from the dropping funnel over 9 hours keeping the temperature at 140°–150°; the reaction mass was heated for a further 32 hours. After this time the reaction mass weighed 565.6 g. The liquor was decanted from the unreacted tin and the tin washed with acetone and dried, leaving a residue of 19.1 g of tin. The decanted liquor (536.7 g) was in two layers and these were separated. The top layer (109

TABLE IV

| | Starting Materials | | | Products Bu$_3$SnBr and Bu$_2$SnBr$_2$ | | | |
|---|---|---|---|---|---|---|---|
| Exp. No. | Cell Bottom phase Kg | BuBr Kg | Elemental Tin Kg | Weight Kg | % Bu$_3$SnBr | % Bu$_2$SnBr$_2$ | Halogenotin Complex By-product, Kg |
| A | 6.4 (after drying) | 2.3 | 0 | 1.74 | 71 | 26 | 6.3 |
| B | 6.56 | 1.68 | .33 | 1.67 | 84 | 7 | 6.9 |
| C | 7.6 | 1.81 | .19 | 1.51 | 85 | 15 | 7.66 |
| Totals | 20.56 | 5.79 | 0.52 | 4.92 | 79.7 | 16.2 | 20.86 |

EXAMPLE 16

Granulated tin (118.7 g, 1 mole) and tetrabutylammonium bromide (Bu$_4$NBr, 161 g, 0.5 mole) were heated to 130°–145° in a flask fitted with a condenser, thermometer and dropping funnel. Butyl chloride (138.7 g, 1.5 mole) was added slowly so that the temperature remained at 130°–145°; this took about 60 hours. After this time the reaction mass weighed 397 g. The liquor was decanted from the unreacted tin and the tin washed with acetone and dried leaving a residue of 39 g of tin. The decanted liquor (342 g) was extracted with hydrocarbon (b.p. 145°–160°, 2×400 ml) leaving a hyg) analysed at 19.6% tin and 14.4% bromine.

The calculated values for trioctyltin bromide are 22.1% tin and 14.9% bromine.

The bottom layer was extracted with hydrocarbon (b.p. 145°–160°, 2×200 ml) leaving a hydrocarbon insoluble residue (340.3 g) which analysed at 20.3% tin and 33% bromine. The hydrocarbon extracts were combined and the hydrocarbon distilled leaving an organotin residue (63 g). This analysed at 21.7% tin and 16.9% bromine. The calculated values for trioctyltin bromide are 22.1% tin and 14.9% bromine.

EXAMPLE 19

Granulated tin (19.5 g, 0.16 mole) tetraoctylammonium bromide (45 g, 0.08 mole) and octyl bromide (47.6 g, 0.24 mole) were heated to 140°–150° for approximately 20 hours in a flask fitted with a thermometer and condenser. After this time the reaction mass weighed 112 g. The liquor was decanted from the unreacted tin and this tin washed with acetone and dried, leaving a residue of 2.7 g of tin. The decanted liquor was extracted with hydrocarbon (b.p. 145°–160°, 2×100 ml) leaving a hydrocarbon insoluble residue 103 g) which analysed at 14% tin and 22.2% bromine. The hydrocarbon extracts were combined and the hydrocarbon distilled leaving an organotin residue (22 g) which analysed at 21.7% tin and 16.4% bromine The calculated values for trioctyltin bromide are 22.1% tin and 14.9% bromine.

EXAMPLE 20

Granulated tin (95 g, 0.8 mole) butyltriphenylphosphonium bromide (80 g, 0.2 mole), butyl bromide (82 g, 0.6 mole), and dimethyl formamide (105 g) were heated in a flask (fitted with a condenser and thermometer) to 150°–155° for approximately 40 hours. After this time the reaction mass weighed 349 g. The liquor was decanted from the unreacted tin and the tin washed with acetone and dried leaving a residue of 58.4 g of tin. The decanted liquor (283 g) was heated in a rotary evaporator under vacuum leaving a liquid residue weighing 186 g. 180 g of this were extracted with hydrocarbon (b.p. 145°–160°, 2×150 ml) leaving a hydrocarbon insoluble residue (156 g) which analysed at 20% tin and 30.4% bromine. The hydrocarbon extracts were combined and the hydrocarbon distilled leaving an organotin residue (19.2 g).

This organotin product analysed at 31.5% tin and 18.7% bromine. The calculated values for tributyltin bromide are 32.1% tin and 21.6% bromine.

EXAMPLE 21

Granulated tin (237.4 g, 2 mole), triphenyl phosphine (131 g, 0.5 mole), and dimethyl formamide (160 g) were heated to 140°–150° in a flask fitted with a condenser, thermometer and dropping funnel. Butyl bromide (274.5 g, 2 mole) was added from the dropping funnel while maintaining the temperature at about 140°. The reaction mass was kept at 140° for approximately 30 hours after which time it weighed 765 g. The liquor was decanted from the unreacted tin which was then washed with acetone and dried, leaving a residue of 138.3 g of tin. The decanted liquor (618.5 g) was distilled under vacuum on a rotary evaporator leaving a liquid residue weighing 476 g. This was extracted with hydrocarbon (b.p. 145°–160°, 2×400 ml), leaving a hydrocarbon insoluble residue (368.5 g) which analysed at 21% tin and 34.8% bromine. The hydrocarbon extracts were combined and the hydrocarbon distilled leaving an organotin residue (81.7 g).

This organotin product analysed at 33% tin and 18.6% bromine. The calculated values for tributyltin bromide are 32.1% tin and 21.6% bromine.

EXAMPLE 22

Granulated tin (118.7 g, 1 mole) and tetrabutylammonium bromide (161 g, 0.5 mole) were heated to 140°–150° in a flask fitted with a condenser, thermometer, and dropping funnel. Propyl bromide (184.5 g, 1.5 mole) was added from the dropping funnel while maintaining the temperature at about 140°, taking about 15 hours. The reaction mass was kept at 140° for approximately 40 hours after which time it weighed 434 g. The liquor was decanted from the unreacted tin which was washed with acetone and dried leaving a residue of 16 g of tin. The decanted liquor was extracted twice on its own volume of hydrocarbon (b.p. 145°–160°) leaving a hydrocarbon insoluble residue (293 g) which analysed at 23.5% tin and 39.2% bromine.

The combined hydrocarbon extracts were distilled to remove the hydrocarbon leaving an organotin residue (65 g) which analysed at 37.6% tin and 24.7% bromine. The calculated values for tripropyltin bromide are 36.2% tin and 24.4% bromine.

EXAMPLE 23

Granulated tin (79 g, 0.67 mole) tetrabutylammonium bromide (107 g, 0.34 mole), and stearyl bromide ($C_{18}H_{37}Br$, 333 g, 1 mole) were heated to 140°–150° in a flask fitted with a condenser and thermometer for about 100 hours. The liquor (which was two phases) was decanted from the unreacted tin which was then washed in the acetone and dried leaving a residue of 14.5 g of tin. The decanted liquor was separated into two phases; the top layer (121 g) analysed at 9% tin. The bottom layer was extracted twice with its own volume of hydrocarbon (b.p. 145°–160°) leaving a hydrocarbon insoluble residue (288 g) which analysed at 16.8% tin and 27.7% bromine. The combined hydrocarbon extracts were distilled to remove the hydrocarbon leaving a residue which analysed at 8.1% tin. 51 g of the top layer of the reaction mass was heated to 70° with ethanol (250 ml) and the bottom layer run off and reheated with a further portion of ethanol (250 ml). The bottom layer from this was dried at 90° under vacuum leaving an organotin residue (29 g).

This organotin product analysed at 12.2% tin and 7.2% bromine. The calculated values for tristearyl tin bromide are 12.4% tin and 8.3% bromine. The ethanol extracts were combined and the ethanol distilled leaving a residue (20 g) which contained 5.0% tin and was probably mainly unreacted stearyl bromide.

EXAMPLE 24

Granulated tin (79 g, 0.67 mole), $Bu_4NBr$ (107 g, 0.34 mole), tetrabutyl ammonium bromostannite ($Bu_4NSnBr_3$ prepared from $Bu_4NBr$ and aqueous $HSnBr_3$, 200 g, 0.34 mole), and copper powder (0.4 g, 0.006 mole) were heated to 140°–150° in a flask fitted with a condenser, thermometer and dropping funnel. Butyl bromide (137 g, 1 mole) was added from the dropping funnel over 2.5 hours keeping the temperature at about 140°. Heating was continued for a further 72 hours by which time the reaction mass weighed 517 g. The liquor was decanted from the unreacted tin and the tin washed with acetone and dried, leaving a residue of 9.1 g of tin. The decanted liquor (494 g) was extracted twice with its own volume of hydrocarbon (b.p. 145°–160°) leaving a hydrocarbon insoluble residue (425 g) which analysed at 17.1% tin and 37% bromine. The hydrocarbon extracts were combined and the hydrocarbon distilled leaving an organotin residue (58.3 g).

This organotin product analysed at 34.8% tin and 24.2% bromine. The calculated values for tributyltin bromide are 32.1% tin and 21.6% bromine.

EXAMPLE 25

Granulated tin (59.4 g, 0.5 mole), tetrabutylammonium iodide (92.5 g, 0.25 mole), and Bu$_4$NSnBr$_3$ (from Bu$_4$NBr and aqueous HSnBr$_3$, 150 g, 0.25 mole) were heated to 140°-150° in a flask fitted with a condenser, thermometer and dropping funnel. Iodobenzene (153 g, 0.75 mole) was added dropwise over 1.5 hours at about 140° and the reaction mass maintained for a further 168 hours at about 140°. After this time the reaction mass weighed 445 g. The liquor was decanted from the unreacted tin which was then washed with acetone and dried, leaving a residue of 33 g of tin. The decanted liquor (360 g) was extracted twice with its own volume of hydrocarbon (b.p. 145°-160°) leaving a hydrocarbon insoluble residue (240 g) which analysed at 18.1% tin, 19% iodine and 19% bromine. The hydrocarbon extracts were combined and the hydrocarbon distilled leaving an organotin residue (12.4 g).

This organotin product analysed at 27.6% tin, 9.5% iodine and 10.2% bromine. The calculated values for a mixture of 60% triphenyltin bromide and 40% triphenyltin iodide are 26.5% tin, 11.2% bromine and 10.6% iodine.

EXAMPLE 26

Granulated tin (118.7 g, 1 mole), and Bu$_4$NBr (161 g, 0.5 mole) were heated to 140°-150° in a flask fitted with a condenser, thermometer and dropping funnel. Benzyl chloride (190 g, 1.5 mole) was added dropwise while keeping the temperature at 140°-150°, taking 12 hours. The reaction mixture was heated for a further 100 hours after which time it weighed 463 g. The liquor was decanted from the unreacted tin and the tin washed with acetone and dried, leaving a residue of 18.2 g of tin. The decanted liquor (440 g) was extracted twice with its own volume of hydrocarbon (b.p. 145°-160°) leaving a hydrocarbon insoluble reside (355 g) which analysed at 30.2% tin. The hydrocarbon extracts were combined and the hydrocarbon distilled leaving an organotin residue (42 g). This organotin product contained both liquid (10 g) and solid (32 g), the liquid analysed at 12.7% tin and the solid at 17.1% tin.

The hydrocarbon insoluble portion (256 g) was further extracted with xylene (3×250 ml) leaving a xylene insoluble residue (206 g) analysing at 30.7% tin, 13.4% chlorine and 11.1% bromine.

The xylene extracts were combined and distilled leaving an organotin residue (40 g) analysing at 22.1% tin, 7.8% chlorine and 7% bromine. The calculated values for a mixture of 75% tribenzyltin chloride and 25% tribenzyltin bromide are 27% tin, 6.2% chlorine and 4.2% bromine.

From the foregoing examples and description it will be apparent to those skilld in the art that this invention may be practiced in a variety of ways and in additional embodiments. Thus various reactants within the general formulae RX and Cat$^+$X$^-$ may be employed in the liquid state, e.g., molten or with an inert solvent, and at varying temperatures. (Of course, an effective amount of solubility of the reagents is required; for instance, for low boiling RX species an adequate superatmospheric pressure may be employed for this purpose.) The choice of these conditions will be made in each instance according to the final product desired, the relative cost of starting materials, and the yield and efficiency sought. Important in each instance, however, will be the features that the reaction will be conducted in the liquid phase (either molten or solution, thus setting a lower temperature limit) and below the decomposition point of the respective reagents employed and products desired. Also, of course, as described above, it is of primary importance to observe the requirements for the presence of a reagent concentration of the 'onium compound represented by Cat$^+$X$^-$ as defined above (and/or of the halogenotin complex by-products), which collaterally means a relatively low concentration (at any point in time) of the RX reagent, i.e., a relatively high amount of Cat$^+$X$^-$. This, of course, generally means a controlled slow addition of the RX reagent to maintain that requirement (unless a system with a very large initial amount of Cat$^+$X$^-$ is used, which is usually a more costly approach and hence not presently preferred). It is also desirable that the molar ratio of tin to RX consumed in the course of the reaction should be at least 2:3, advantageously at least 1:1.

Further, while the production of triorganotin oxides from the triorganotin halides has been illustrated (e.g., Example 10), it will be appreciated that in general compounds of the formula R$_3$SnX (where X is halogen) produced herein may be similarly converted with the appropriate agent to compounds of the general formula R$_3$SnY, where Y represents other anionic species, such as sulfides, borate, carboxylate, sulfate, phosphate, nitrates, or phenolates such as pentachloro phenolate, etc.

Accordingly, this invention is limited solely by the spirit and scope of the following claims:

What we claim is:

1. A process for the prredominant production of triorgano tin halides by the direct reaction of elemental tin with an organic halide to produce organo tin halides of the general formula:

$$R_aSnX_{(4-a)}$$

wherein
- each R independently represents a hydrocarbyl radical covalently bonded to tin;
- each X independently represents any chloride, bromide or iodide; and
- a may be a number from 1 to 3, but in the majority is 3;

which process comprises reacting an organic halide of the formula RX added during the course of the reaction with a molar excess, relative thereto, of elemental tin in the presence of a reagent amount of an 'onium compound at an elevated temperature sufficient to maintain the same in the liquid state, while also maintaining the weight and molar concentration of said 'onium compound relative to said RX throughout the reaction period at a molar ratio of at least 1:5, whereby there is obtained an organo tin halide product having R$_3$SnX as the molar predominant molecular species, while also forming as a by-product a water-insoluble halogeno tin complex with the 'onium cation.

2. A process for the predominant production of triorgano tin halides by the direct reaction of elemental tin with an organic halide to produce organo tin halides of the general formula:

$$R_aSnX_{(4-a)}$$

wherein
- each R independently represents a hydrocarbyl radical covalently bonded to tin;
- each X independently represents any chloride, bromide or iodide; and
- a may be a number from 1 to 3, but in the majority is 3;

which process comprises reacting an organic halide of the formula RX, added during the course of the reaction, with a molar excess, relative thereto, of elemental tin in the presence of a reagent amount of $$Cat^+X^-$$

wherein $Cat^+$ represents a quaternary cation radical of nitrogen, phosphorus, arsenic or antimony, or of a ternary positively-charged radical of sulfur or selenium, or of an alkali or alkaline earth metal complex of diglyme, polyalkyleneglycol, glycol ether, or of a crown ether; and each $X^-$ independently represents any of chloride, bromide or iodide ions, while maintaining the weight and molar concentration of $Cat^+X^-$ relative to said RX throughout the reaction period at a molar ratio of at least 1:5, whereby there is obtained an organo tin halide product having as the molar predominant molecular species of the formula $R_3SnX$ while also forming, as a by-product, a water-insoluble halogeno tin $Cat^+$ complex.

3. A process according to claim 1 wherein said ratio is at least 1:3.

4. A process according to claim 1 wherein the molar ratio of said elemental tin to the RX consumed throughout the reaction is at least 2:3.

5. A process according to claim 2 wherein said ratio is at least 1:3.

6. A process according to claim 2 wherein the molar ratio of said elemental tin to the RX consumed throughout the reaction is at least 2:3.

7. A process according to claim 2, wherein said reaction is conducted at a temperature above the melting point of said liquid state $Cat^+X^-$ and below the decomposition point of said $Cat^+X^-$ or RX.

8. A process of claim 5 wherein said $Cat^+$ has the general formula $$R'_zQ^+$$

wherein

Q represents a nitrogen, arsenic or antimony atom, in which case z represents 4, or Q represents sulfur or selenium, in which case z represents 3, and each R' represents independently a hydrocarbyl organic group, including a divalent hydrocarbyl or oxyhydrocarbyl radical representing 2R' and forming, with Q, a heterocyclic ring.

9. A process according to claim 2 wherein said organotin halide is separated from said complex product by solvent extraction.

10. A process according to claim 9 wherein an extracted organotin halide solvent mixture is further reacted with alkali to form the corresponding organotin oxide of the formula $$(R_aSn)_2O$$

and an inorganic halide by-product.

11. A process according to claim 10 wherein said organotin oxide has the formula $(R_3Sn)_2O$.

12. A process of claim 10 wherein said inorganic halide is reacted with ROH to form RX for use as starting material in said process for making $R_aSn_{(4-a)}$.

13. A process of claim 2 wherein R represents a radical of up to 20 carbon atoms of the class of alkyl, cycloalkyl, alkenyl, alkaryl, aralkyl, aralkenyl radicals.

14. A process according to claim 2 wherein said complex by-product is formed in substantially equimolar amount, based on tin, with said $R_aSnX_{(4-a)}$ product.

15. A process according to claim 2 wherein said $Cat^+X^-$ reagent is obtained from an at least two-phase electrolysis method using the water-insoluble halogenotin $Cat^+$ complex by-product as catholyte and an aqueous halide solution as immiscible anolyte.

16. A process according to claim 15 wherein dendritic tin formed in said electrolysis method is used as said elemental tin.

* * * * *